US008503790B2

(12) United States Patent
Ito et al.

(10) Patent No.: US 8,503,790 B2
(45) Date of Patent: Aug. 6, 2013

(54) IMAGE-PROCESSING METHOD, IMAGE-PROCESSING PROGRAM AND IMAGE-PROCESSING DEVICE FOR PROCESSING TIME-LAPSE IMAGE

(75) Inventors: Kei Ito, Okegawa (JP); Masafumi Mimura, Ageo (JP)

(73) Assignee: Nikon Corporation, Tokyo (JP)

( * ) Notice: Subject to any disclaimer, the term of this patent is extended or adjusted under 35 U.S.C. 154(b) by 128 days.

(21) Appl. No.: 12/801,666

(22) Filed: Jun. 18, 2010

(65) Prior Publication Data
US 2010/0260422 A1 Oct. 14, 2010

Related U.S. Application Data

(63) Continuation of application No. PCT/JP2008/073039, filed on Dec. 18, 2008.

(30) Foreign Application Priority Data

Dec. 20, 2007 (JP) ................................ 2007-328471

(51) Int. Cl.
*G06K 9/46* (2006.01)
(52) U.S. Cl.
USPC ......... 382/190; 348/208.1; 348/263; 382/133
(58) Field of Classification Search
USPC ................ 348/208.1, 263, 265; 382/133, 190
See application file for complete search history.

(56) References Cited

U.S. PATENT DOCUMENTS

| 6,784,927 B1 * | 8/2004 | Itokawa ..................... 348/208.1 |
| 7,630,628 B2 * | 12/2009 | Ogihara ........................ 396/432 |
| 7,847,843 B2 * | 12/2010 | Suda ............................. 348/263 |
| 2002/0122124 A1 * | 9/2002 | Suda ............................. 348/263 |
| 2007/0070498 A1 * | 3/2007 | Endo et al. .................... 359/434 |
| 2007/0242899 A1 * | 10/2007 | Satoh et al. ................... 382/286 |
| 2008/0279441 A1 * | 11/2008 | Matsuo et al. ................ 382/133 |

FOREIGN PATENT DOCUMENTS

| JP | 2005-164707 | 6/2005 |
| JP | 2006-23494 | 1/2006 |

OTHER PUBLICATIONS

International Search Report for PCT/JP2008/073039, mailed Feb. 3, 2009.

* cited by examiner

*Primary Examiner* — Gregory M Desire

(57) ABSTRACT

An image-processing method for processing a time lapse image includes acquiring a first image obtained by capturing an image of an object located within a field of view using an imaging device and a second image obtained by capturing an image of the object located within the field of view using the imaging device after a predetermined time period has elapsed, calculating a positional correction value for a positional shift between the first image and the second image, by using a correlation function weighted according to an image feature of each of the objects included in the first image and the second image, and performing, based on the calculated positional correction value, a positional correction between the first image and the second image. The time lapse image is generated using the first image and the second image on which the positional correction has been performed.

12 Claims, 8 Drawing Sheets

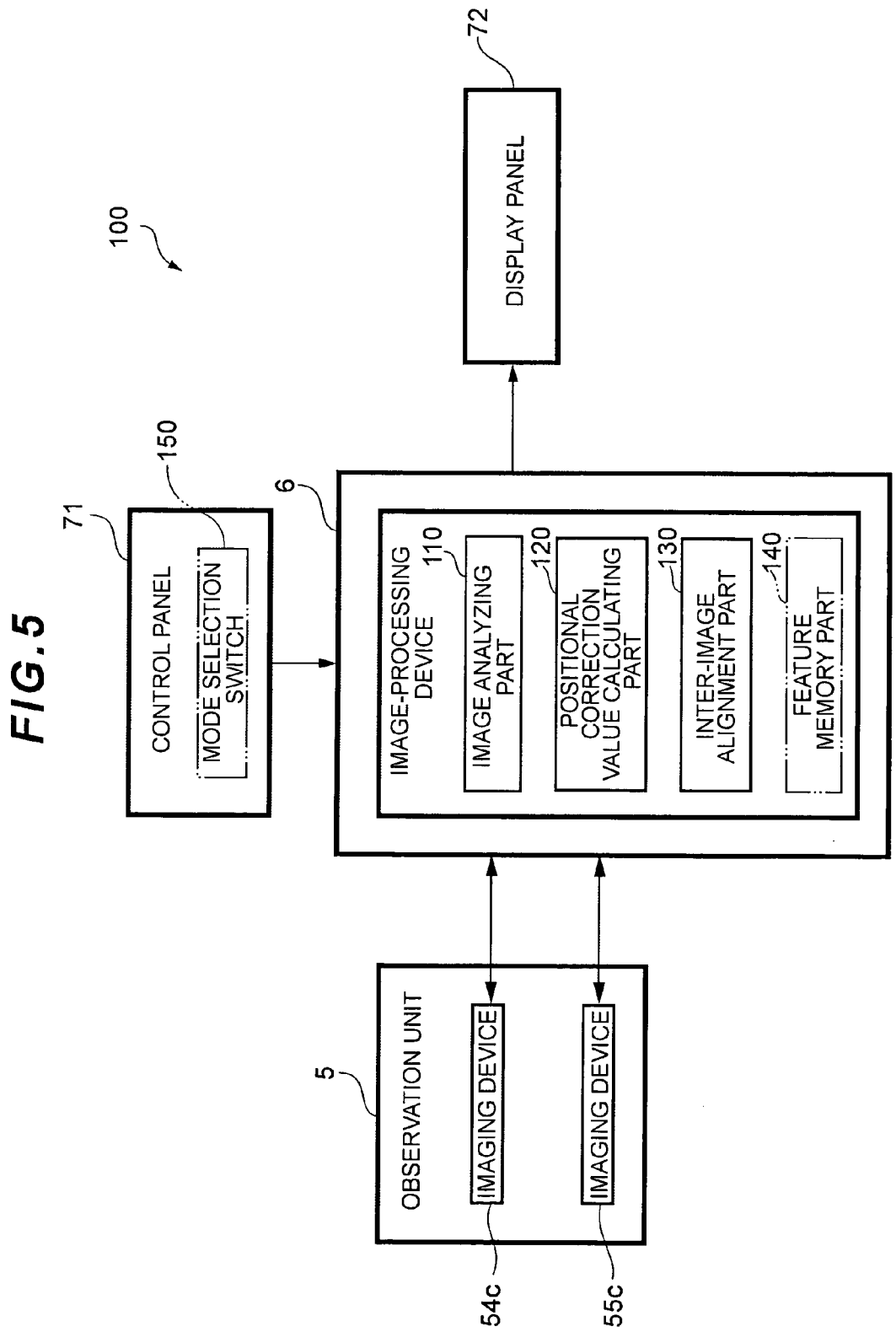

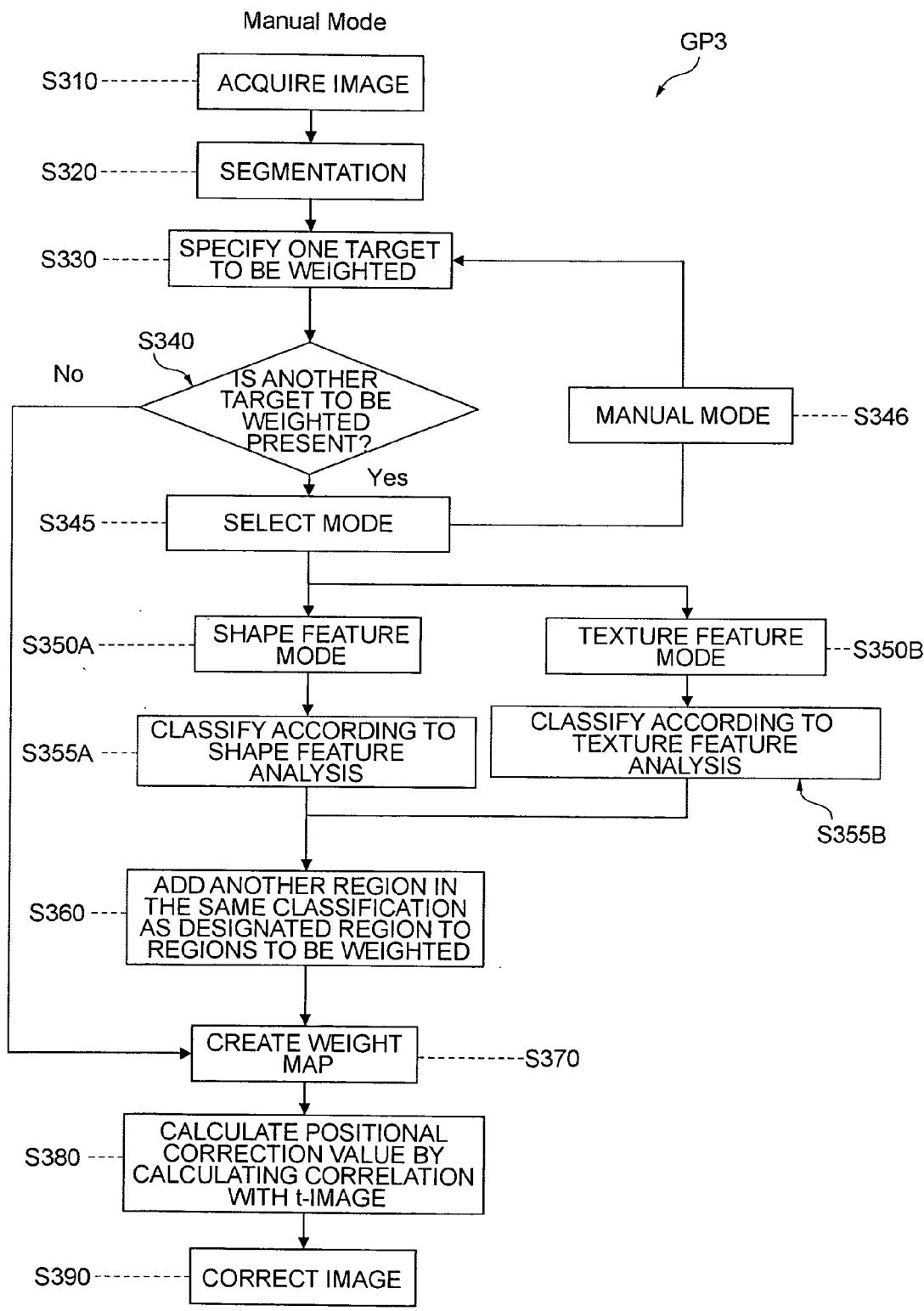

IMAGE-PROCESSING METHOD, IMAGE-PROCESSING PROGRAM AND IMAGE-PROCESSING DEVICE FOR PROCESSING TIME-LAPSE IMAGE

CROSS-REFERENCE TO RELATED APPLICATIONS

This is a continuation application, under 35 U.S.C. 111(a), of PCT International Application No. PCT/JP2008/073039, filed on Dec. 18, 2008, which is hereby incorporated by reference. This application also claims the benefit of Japanese Patent Application No. 2007-328471, filed in Japan on Dec. 20, 2007, which is hereby incorporated by reference.

TECHNICAL FIELD

The present invention relates to image-processing means for processing a time-lapse image, the image-processing means used for intermittently capturing an image of an observed object at predetermined time intervals using an imaging device and acquiring a plurality of images, and for arranging the obtained images in chronologically and generating a time-lapse image.

TECHNICAL BACKGROUND

Cell culture microscopes for observing changes in state while cultivating live cells, and observation devices for observing road or maritime traffic congestion conditions and the like, are types of apparatuses such as the one described above for using a time-lapse image to observe changes in an observed object. In an apparatus of such description, taking a cell culture microscope as an example, in order to observe the motion states of individual cells or between cells and perform an appropriate evaluation, it is necessary to verify the spatial position of each cell in a field of view using hardware or software means and generate a time-lapse image.

In order to verify the spatial position of each of the cells in the field of view, i.e., the relative positions of the observed object and the observation optical system that includes the imaging device, by hardware means using a mechanism configuration, it is necessary to provide an alignment optical system for positional correction or use Super Invar, a ceramic, or another costly material having an extremely low thermal expansion coefficient to constitute the members in order to minimize the effects of temperature drift; so that the entire apparatus increases in complexity and cost. Also, in order to minimize the relative positional shift between the observation optical system and the observed object, it is necessary to fix the relative positions of the observation optical system and the observed object and to continue observing the same observed object. In order to avoid such disadvantages and make it possible to observe a plurality of observed objects while exchanging the observed objects as appropriate, there has been proposed a method for correlating intermittently captured images as a whole, whereby positional correction between images is performed by software means (see e.g., patent document 1).

Patent Document: 1 Japanese Laid-open Patent Application No. 2006-23494

SUMMARY OF THE INVENTION

In an instance where positional correction is performed by obtaining a correlation of an image as a whole between respective images, it is necessary to presume that each of the individual cells in the field of view is moving randomly, and that the center of gravity of the whole image is stationary. Therefore, in an instance where, for example, foreign objects, bubbles, or other articles that do not form part of the observed object travel through the field of view, problems have been presented in that the assumption of random movement may be compromised, and the positional correction may be affected by the displacement of the object that does not form part of the observed object.

With the foregoing aspects of the prior art in view, it is an object of the present invention to provide image-processing means for processing time-lapse images in which an enhancement is made to the accuracy of positional correction between each of the intermittently captured images.

According to a first aspect of the present invention, there is provided an image-processing method for processing a time-lapse image, comprising: acquiring a first image obtained by using an imaging device to capture an image of a plurality of objects (e.g., cells $C1$, $C2$ in an embodiment) located within a field of view, and the second image being obtained by using the imaging device to capture an image of the objects located within the field of view after a predetermined time period has elapsed; calculating a positional correction value to be used for a relative shift in the position in which the first image and the second image are captured by using a correlation function weighted according to an image feature of each of the objects included in the first image and the second image; and performing a positional correction between the first image and the second image based on the positional correction value, and generating a time-lapse image.

According to a second aspect of the present invention, there is provided an image-processing program for processing a time-lapse image, comprising the steps of: acquiring a first image obtained by using an imaging device to capture an image of a plurality of objects located within a field of view and a second image obtained by using the imaging device to capture an image of the plurality of objects (e.g., cells $C1$, $C2$ in the embodiment) located within the field of view after a predetermined time period has elapsed; calculating a positional correlation value to be used for a relative shift in the position in which the first image and the second image are captured by using a correlation function weighted according to an image feature of each of the objects included in the first image and the second image; performing a positional correction between the first image and the second image based on the calculated positional correction value; and generating a time-lapse image using the first image and the second image between which the positional correction has been performed.

According to a third aspect of the present invention, there is provided an image-processing device for processing a time-lapse image, comprising: an imaging device capturing an image of a plurality of objects; an image analyzing part analyzing, from a first image and a second image captured by the imaging device at a predetermined time interval, an image feature of each of the objects (e.g., cells $C1$, $C2$ in the embodiment) included in each of the images; a positional correction value calculating part calculating a positional correction value to be used for a relative shift in the position in which the first image and the second image are captured, using a correlation function weighted according to the analyzed image feature of each of the objects; and an inter-image alignment part performing, based on the positional correction value calculated by the positional correction value calculating part, a positional correction between the first image and the second image wherein a time-lapse image is generated using the first image and the second image between which the positional correction has been performed by the inter-image alignment part.

According to the image-processing method, image-processing program, and image-processing device for processing time-lapse images of the above description, positional correction between each of a plurality of images is calculated using a correlation function weighted according to the image feature of each of the objects located in the field of view, making it possible to provide image-processing means for processing time-lapse images in which an enhancement is made to the accuracy of positional correction between each of the intermittently captured images.

BRIEF DESCRIPTION OF THE DRAWINGS

FIG. 5 is a block diagram schematically showing an image-processing device;

FIG. 8 is a flowchart showing an image-processing program according to a third embodiment.

EXPLANATION OF NUMERALS AND CHARACTERS

Figure 1:
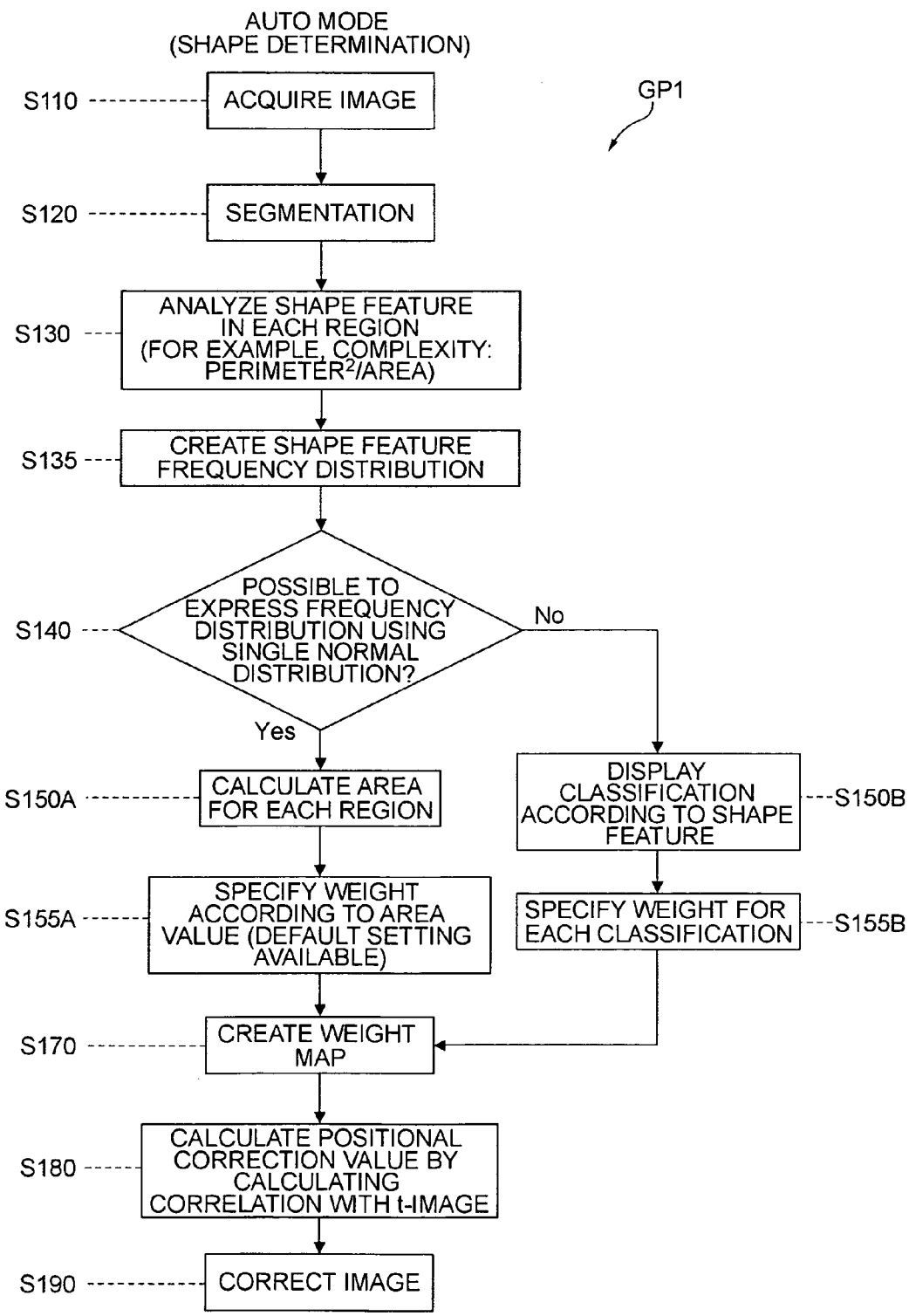
FIG. 1 is a flowchart showing an image-processing program according to a first embodiment.

BS Cell culture observation system
C1, C2 Cell (object)
GP (GP1 through GP3) Image-processing program
Microscopy system (55c: imaging device)
100 (101 through 103) Image-processing device
110 Image-analyzing part
120 Positional correction value calculating part
130 Inter-image alignment part
140 Feature memory part
150 Mode selection switch (mode selection means)

DESCRIPTION OF THE PREFERRED EMBODIMENTS

Figure 2:
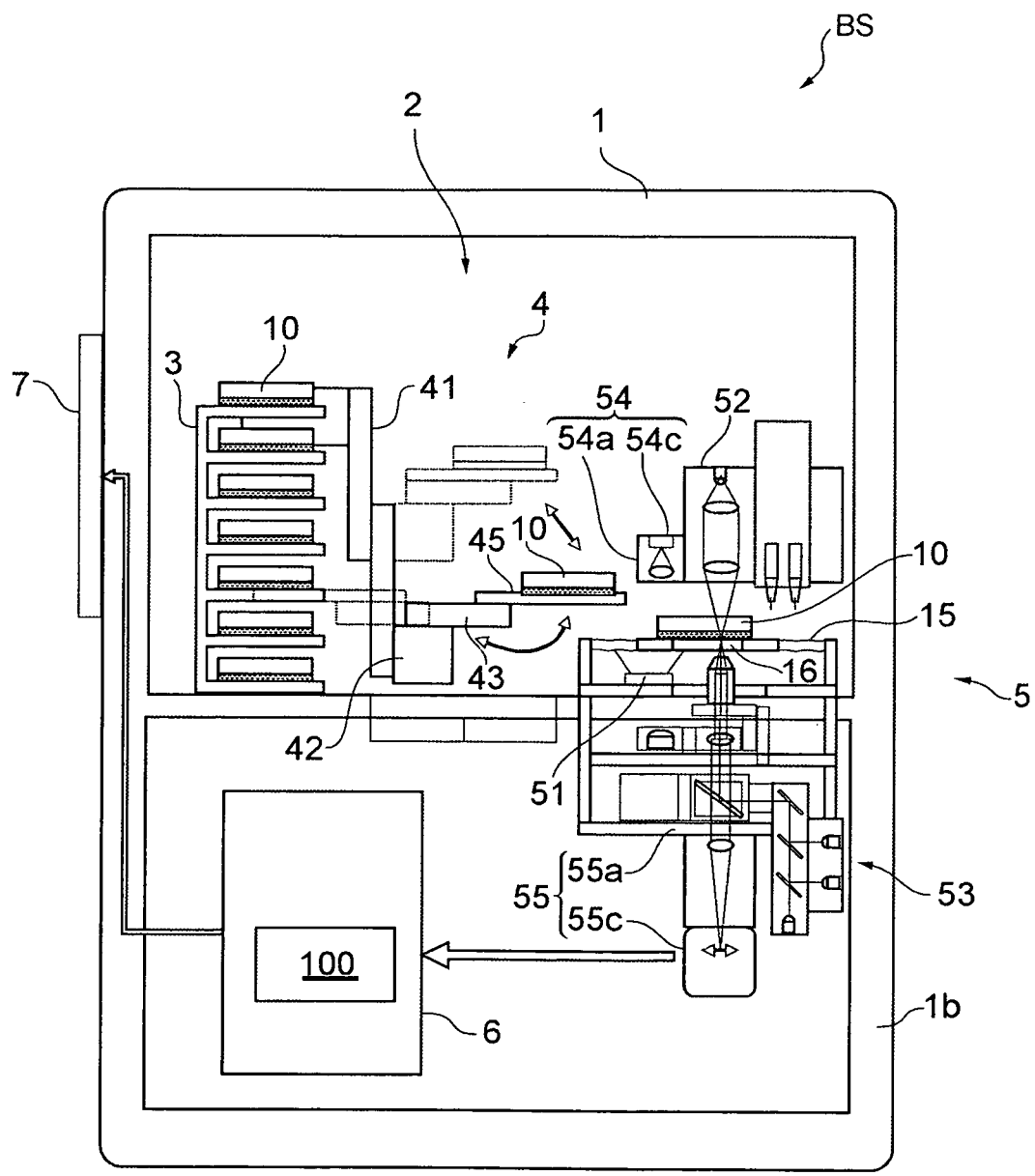
FIG. 2 is a schematic diagram showing a cell culture observation system shown as an example of an application of the present invention.
Figure 3:
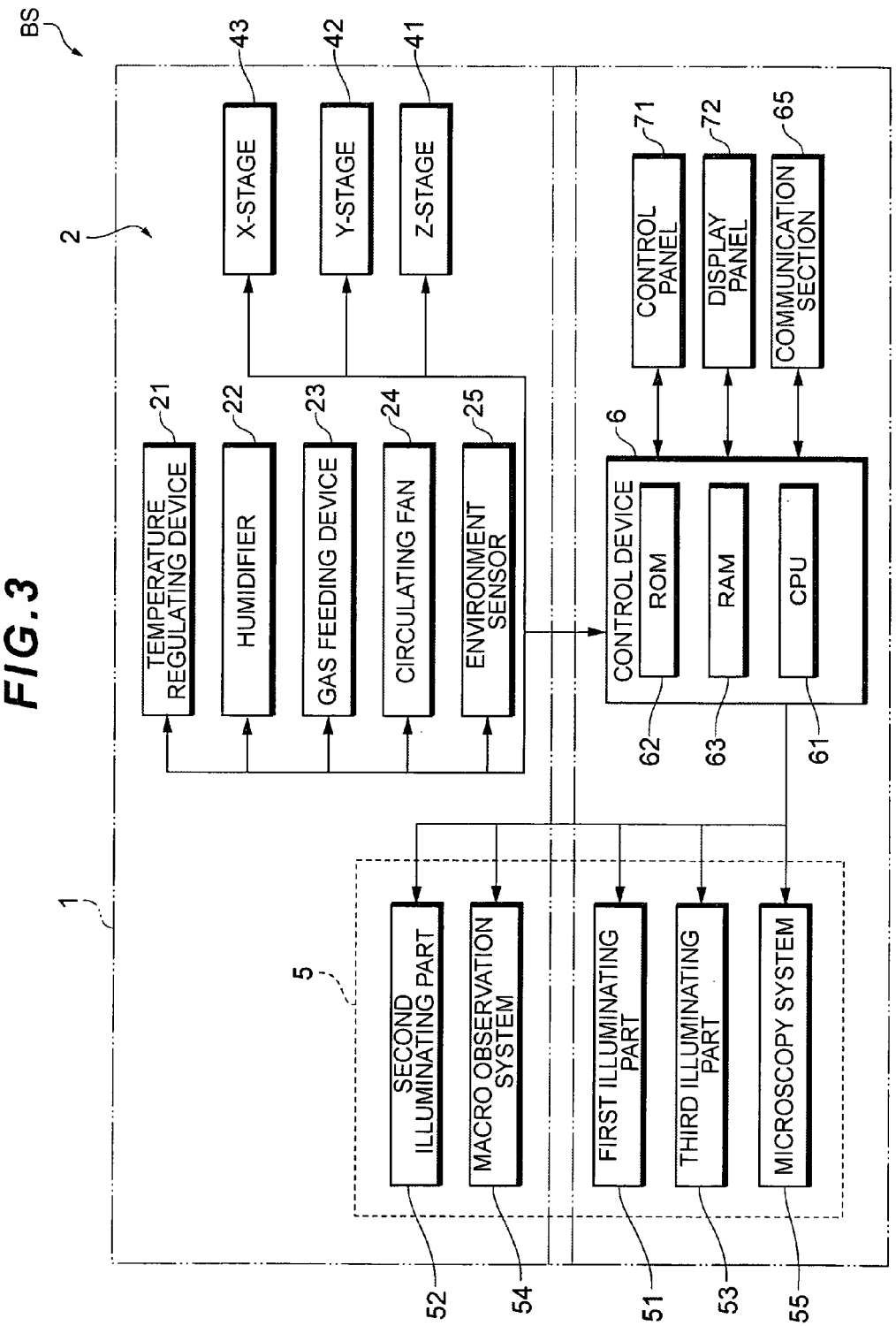
FIG. 3 is a block diagram showing the cell culture observation system.

Preferred embodiments will now be described with reference to the drawings. FIGS. 2 and 3 respectively show a schematic diagram and a block diagram of a cell culture system as an example of a system in which an image-processing device is used for processing time-lapse images according to the present invention.

The cell culture observation system BS broadly comprises a culture chamber 2 provided to an upper portion of a case 1; a rack-shaped stocker 3 for accommodating and holding a plurality of culture containers 10; an observation unit 5 for observing a sample in a culture container 10; a conveying unit 4 for conveying the culture container 10 between the stocker 3 and the observation unit 5; and a control board 7 having an image display device.

The culture chamber 2 is a chamber in which is formed and maintained a culture environment according to the type, purpose, or other attribute of the cell to be cultured. In order to prevent environmental variation or contamination, the culture chamber 2 is kept in a sealed state after a sample has been introduced thereinto. A temperature regulating device 21 for increasing or decreasing the temperature within the culture chamber; a humidifier 22 for regulating humidity; a gas feeding device 23 for feeding $CO_2$ gas, $N_2$ gas, or another gas; a circulating fan 24 for creating a uniform environment throughout the culture chamber 2; an environment sensor 25 for detecting the temperature, the humidity, and other conditions within the culture chamber 2; and similar devices are provided in association with the culture chamber 2. The operation of each of the devices is regulated by a control unit 6, and a culture environment specified by the temperature, humidity, carbon dioxide concentration, and other conditions in the culture chamber 2 is kept in a state that matches a culture condition set using the control board 7.

As shown in FIG. 2, the stocker 3 is formed to a shape of a rack having a plurality of partitions in the vertical direction and the depth direction running perpendicular to the plane of the diagram. Each rack is assigned a unique address; for example, in an instance where the stocker 3 is divided into columns A through C in the depth direction and rows 1 through 7 in the vertical direction, a rack located at column A, row 5 is assigned an address of A-5.

The culture container 10 may be a flask, a dish, a well plate, or another type of container varying in size and shape, such as round or rectangular. An appropriate culture container 10 may be selected and used in accordance with the type and purpose of the cell to be cultured. A configuration using a dish is shown as an example in the present embodiment. A cell or another sample is injected into the culture container 10 together with a liquid culture medium containing phenol red or another pH indicator. The culture container 10 is given a code number and accommodated in a corresponding specified address in the stocker 3. The culture container 10 is accommodated and stored in each of the racks in a state in which a container holder used for conveyance is attached, the container holder being formed according to the type, format, and similar attributes of the container.

The conveying unit 4 comprises a Z-stage 41, provided within the culture chamber 2 so as to be moveable along the vertical direction and moved up or down by a Z-axis driving mechanism; a Y-stage 42 attached to the Z-stage 41 so as to be moveable along the depth direction and moved either way by a Y-axis driving mechanism; an X-stage 43 attached to the Y-stage 42 so as to be moveable along the lateral direction and moved either way by an X-axis driving mechanism; and other components. A supporting arm 45 for holding and supporting the culture container 10 is provided at a distal end side of the X-stage 43, which moves in the lateral direction relative to the Y-stage. The conveying unit 4 is configured so that the supporting arm 45 has a movement range that allows movement between all of the racks in the stocker 3 and a sample stage 15 of the observation unit 5. Each of the X-axis driving mechanism, the Y-axis driving mechanism, and the Z-axis driving mechanism comprises, for example, a servo motor having a ball screw and an encoder, the operation of each of which driving mechanisms being controlled by the control unit 6.

The observation unit 5 comprises a first illuminating part 51, a second illuminating part 52, a third illuminating part 53, a macro observation system 54 for performing macro observation of the sample, a microscopy system 55 for performing microscopy of the sample, an image-processing device 100, and other components. The sample stage 15 is made from a translucent material, and is provided with a transparent window section 16 located at a region of observation in the microscopy system 55.

The first illuminating part 51 comprises a surface-emitting light source provided on a side towards a lower frame 1*b*, and illuminates the whole of the culture container 10 from below the sample stage 15 in the form of backlight illumination. The second illuminating part 52, provided in the culture chamber 2, has an LED or another light source and an illumination optical system comprising a phase ring, a condenser lens, or a similar component; and illuminates the sample in the culture container from above the sample stage 15 and along an optical axis of the microscopy system 55. The third illuminating part 53 has a plurality of LEDs, mercury lamps, or light sources of another type, each of which used for emitting light of a wavelength that is suitable for epi-illumination observation or fluorescence observation; and an illumination optical system comprising a beam splitter, a fluorescence filter, or another device for superimposing light emitted from each of the light sources onto the optical axis of the microscopy system 55. The third illuminating part 53, provided within the lower frame 1*b* located below the culture chamber 2, illuminates the sample in the culture container from below the sample stage 15 and along an optical axis of the microscopy system 55.

The macro observation system 54, provided in the culture chamber 2 so as to be located above the first illuminating part 51, has an observation optical system 54*a* and a CCD camera or another imaging device 54*c* for capturing an image of the sample formed by the observation optical system. The macro observation system 54 captures an overall observed image (i.e., a macro image) from above the culture container 10 which is backlit by the first illuminating part 51.

The microscopy system 55, provided within the lower frame 1*b*, has an observation optical system 55*a* comprising an objective, a middle zooming lens, a fluorescence filter, and similar components; and a cooled CCD camera or another imaging device 55*c* for capturing an image of the sample formed by the observation optical system 55*a*. Each of the objective and the middle zooming lens is provided in a plural number, and is configured so that a plurality of magnification levels can be set using a revolver, a slider, or another displacement mechanism (not shown in detail). The magnification can be varied between, for example, 2× and 80×, depending on the initially selected lens configuration. The microscopy system 55 captures a microscopically observed picture (i.e., a micro image), obtained by microscopically observing transmitted light illuminated by the second illuminating part 52 and transmitted through the cell, reflected light illuminated by the third illuminating part 53 and reflected by the cell, or fluorescent light emitted by the cell when illumination has been provided by the third illuminating part 53.

The image-processing device 100 performs an analog-to-digital conversion on a signal inputted from the imaging device 54*c* of the macro observation system and the imaging device 55*c* of the microscopy system, performs a variety of types of image-processing, and generates image data for the overall observed image or the microscopically observed image. The image-processing device 100 also performs image analysis on the image data for the observed images, generates a time-lapse image, calculates cell movement, or otherwise analyzes the image data. Specifically, the image-processing device 100 is configured by executing an image-processing program stored in a ROM of the control unit 6 described below. The image-processing device 100 will be described in detail further below.

The control unit 6 comprises a CPU 61; a ROM 62, in which a control program for controlling the operation of the cell culture observation system BS, or data for controlling a variety of components, are configured and stored; a RAM 63 for temporarily storing image data and other data; and other devices. In the control unit 6, the devices are connected by a data bus. Connected to an input/output port of the control unit 6 are the temperature regulating device 21, the humidifier 22, the gas feeding device 23, the circulating fan 24, and the environment sensor 25 provided to the culture chamber 2; each of the X-, Y-, and Z-axis driving mechanisms for driving the X, Y, Z stages 43, 42, 41 provided to the conveying unit 4; the first, second, and third illuminating parts 51, 52, 53, the macro observation system 54, and the microscopy system 55 provided to the observation unit 5; a control panel 71 and a display panel 72 provided to the control board 7; and other devices. A detection signal is inputted from each of the devices listed above into the CPU 61, and each of the devices is controlled in accordance with a control program stored in advance in the ROM 62.

The control panel 71, to which is provided a keyboard, a sheet switch, and an input/output device such as a read/write device for reading information from, and writing information to, a magnetic recording medium, an optical disc, or another medium; and the display panel 72, for displaying a variety of operation screens, image data, and other information, are provided to the control board 7. The user configures an observation program (operating condition), selects conditions, and enters an operation command, or other information using the control panel 71 while referring to the display panel 72, and thereby operates, via the CPU 61, the devices provided to the cell culture observation system BS. In other words, in accordance with what is input from the control panel 71, the CPU 61 adjusts the environment in the culture chamber 2; conveys the culture container 10 within the culture chamber 2; observes the sample using the observation unit 5; analyzes obtained image data; displays information on the display panel 72; and performs other operations. The display panel 72 displays numerical values representing environmental conditions in the culture chamber 2, analyzed image data, alerts in the event of a fault, and the like in addition to operation commands, condition selections, and other input screens. The CPU 61 is able to transmit and receive data to and from an externally connected computer or another device via a communication section 65 compliant with wired or wireless telecommunication standards.

The temperature, humidity, or other environmental conditions in the culture chamber 2; an observation schedule for each of the culture containers 10, the type, position, magnification, and other observation conditions associated with the observation unit 5; and other operation conditions for the observation program configured using the control panel 71 are stored in the RAM 63. The code number for each of the culture containers 10 accommodated in the culture chamber 2, the storage address of the culture container 10 in the stocker 3 corresponding to each code number, and other management data for managing the culture container 10; and a variety of data used for the image analysis are also stored in the RAM 63. The RAM 63 is provided with an image data storage region for storing data relating to captured images obtained using the observation unit 5. Indexing data, containing the code number of the culture container 10, the date and time when the image was captured, and similar information, is stored with the corresponding image data.

In the cell culture observation system BS configured as above, the CPU 61 controls the operation of each of the devices based on the control program stored in the ROM 62 and automatically captures an image of the sample in the culture container 10, according to the conditions set for the observation program as entered using the control board 7. In other words, when operation of the control panel 71 (or remote operation via the communication section 65) starts the observation program, the CPU 61 reads the value of each of the environmental conditions stored in the RAM 63; detects the environmental state in the culture chamber 2 inputted from the environment sensor 25; operates the temperature regulating device 21, the humidifier 22, the gas feeding device 23, the circulating fan 24, and similar devices; and performs feedback control on the temperature, humidity, carbon dioxide concentration, and other culture environment conditions in the culture chamber 2.

The CPU 61 reads the observation conditions stored in the RAM 63, operates each of the X-, Y-, and Z-axis driving mechanisms for driving the X, Y, Z stages 43, 42, 41 provided to the conveying unit 4 and conveys the culture container 10 corresponding to the observed object from the stocker 3 to the sample stage 15 in the observation unit 5 according to an observation schedule, and starts observation of the observed object by the observation unit 5. For example, in an instance where the observation program has been set for macro observation, the culture container 10 conveyed by the conveying unit 4 from the stocker 3 is positioned on an optical axis of the macro observation system 54 and placed on the sample stage 15, the light source of the first illuminating part 51 is illuminated, and the imaging device 54c is used to capture an overall observation picture from above the backlit culture container 10. A signal sent from the imaging device 54c into the control unit 6 is processed by the image-processing device 100, an overall observed image is generated, and the image data is stored in the RAM 63 together with the indexing data, such as the date and time when the image was captured, and other information.

In an instance where the observation program has been set for microscopy of a sample at a specific location in the culture container 10, the specific location in the culture container 10 conveyed by the conveying unit 4 is positioned on an optical axis of the microscopy system 55 and placed on the sample stage 15, the light source of the second illuminating part 52 or the third illuminating part 53 is illuminated, and the imaging device 55c is used to capture a transmission-illuminated, epi-illuminated, or fluorescence-assisted microscopically observed picture. A signal obtained when an image is captured by the imaging device 55c and sent to the control unit 6 is processed by the image-processing device 100, a microscopically observed image is generated, and the image data is stored in the RAM 63 together with the indexing data, such as the date and time when the image was captured, and other information.

The CPU 61 performs the observation described above on a plurality of samples in culture containers accommodated in the stocker 3, wherein the overall observed picture or the microscopically observed picture is successively captured according to an observation schedule having a time interval of about 30 minutes to 2 hours based on the observation program. According to the present embodiment, the time interval between captured images may be fixed or variable. The image data for the overall observed picture or the microscopically observed picture that has been captured is stored with the code number of the culture container 10 in the image data storage region of the RAM 63. The image data stored in the RAM 63 is read from the RAM 63 according to an image display command inputted from the control panel 71, and an overall observed image or a microscopically observed image at a specified time (i.e., a single image), or a time-lapse image of overall observed pictures or microscopically observed pictures from a specified time region, are displayed on the display panel 72 of the control board 7.

Thus, in the cell culture observation system BS, the designated culture container 10 is conveyed by the conveying unit 4 from the stocker 3 to the observation unit 5 according to the observation program setting and positioned on the optical axis of the specified observation system, whereupon an image is captured by the imaging device. Specifically, in the cell culture observation system BS, the sample to be observed and the observation system are moved relative to each other with each observation. It is therefore difficult to match the relative positional relationship between the observed object and the observation system with regards to a plurality of observation cycles; it is particularly difficult at higher observation magnifications. Therefore, the position of an image captured by each of the imaging devices 54c, 55c relative to the sample (i.e., the position of the sample in the field of view) slightly varies between each observation, and the position within the field of view of observation inevitably shifts between each of the images stored in the RAM 63.

Such a positional shift has a significant adverse effect on image quality when a time-lapse image is generated, wherein a large number of intermittently captured images are replayed continuously, and states of change in the sample that are difficult to ascertain visually in the real-time axis, are visualized as dynamic change in the manner of a video image in a compressed time axis. Therefore, a method has conventionally been used where, on the assumption that the observed object is undergoing random motion, a correlation of whole images is obtained with regards to intermittently captured images, and positional correction between the images is performed.

However, foreign objects, bubbles, or other articles that do not form part of the observed object (referred to as non-target objects) may be included along with a cell or other target objects in the field of view of the observation system. In an instance where a non-target object of such description is travelling through the field of view due to the effect of the flow of the culture medium as the culture container 10 is conveyed or of wind generated by the operation of the circulating fan 24, the positional correction may be affected by the displacement of the non-target object.

Even in an instance where the field of view does not contain a non-target object, the cells that are the observed object (i.e., a single cell or a cell cluster) may often vary in size or contain a plurality of cells having varying characteristics. In such an example, when the flow of the culture medium, wind pressure, or another external pressure moves small cells, which are prone to the effects of an external force, or suspension cells over a significant distance, the positional correction may be significantly affected by the movement of the cells.

Figure 4A:
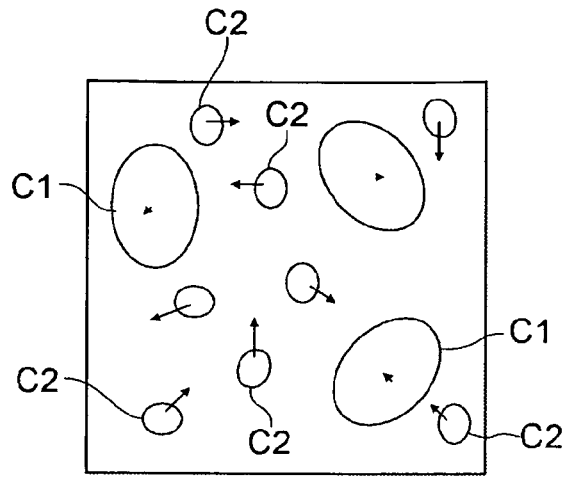
FIG. 4 is a diagram schematically showing a microscopically observed picture shown to illustrate conventional positional correction.
Figure 4B:
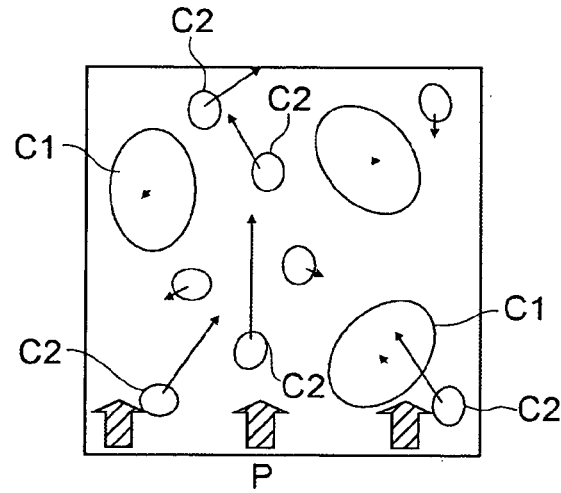
Figure 4C:
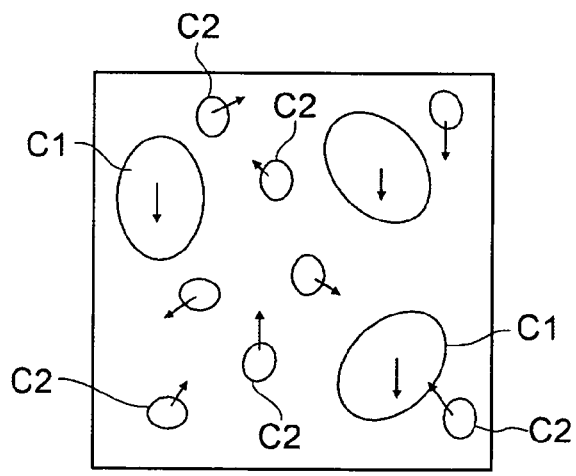

Each of FIGS. 4A through 4C schematically shows a microscopically observed picture that can be seen when a sample containing cells of different sizes is observed using the microscopy system 55, shown in order to illustrate a circumstance in which positional correction as described above is performed. In the drawings, C1 represents a cell having a large area in contact with the culture container, and C2 represents a cell having a small area in contact with the culture container.

FIG. 4A shows a microscopically observed image, captured by the imaging device 55c at a time t, on which positional correction can be performed. Each of the arrows shown in the drawing represents the amount of movement of the cells when observed at a subsequent scheduled observation time t+1. As shown in the drawing, the amount of movement of each of the cells C1 having a large contact area generally tends to be small, and the amount of movement of each of the cells C2 having a small contact area generally tends to be large.

FIG. 4B is a microscopically observed image in an instance where the state shown in FIG. 4A is subject to an external pressure P applied from the bottom to the top of the drawing. As with FIG. 4A, arrows are used to show the amount of movement of the cells when observed at a subsequent scheduled observation time t+1. The cells C2 having a small contact area are more susceptible to the effect of the flow of the culture medium, wind pressure, or another external pressure; and have a larger amount of upward movement compared to the cells C1 having a large contact area. In such an instance, a positional correction amount determined from a correlation value of the whole image between the image at time t and the image at time t+1 is the total value of the positioning error in positioning the observed object relative to the optical axis of the microscopy system 55 and the extent of movement resulting from the effect of the external pressure P.

FIG. 4C is an image in an instance where the amount of movement of each of the cells C1, C2 is calculated from the image at time t, and the image at time t+1 on which positional correction has been performed from the correlation value of the whole of the image shown in FIG. 4B. The positional correction between the images over-corrects the extent of movement resulting from the effect of the external pressure P. Therefore, the calculated amount of movement of small cells C2, which have been moved upwards a considerable amount by the external pressure P, is small, and a downward movement amount is calculated with regards to large cells C1 which, in essence, have not moved by any significant amount.

In order to rectify such a problem, the cell culture observation system BS is configured so that a first image at time t and a second image at time t+1 captured intermittently according to an observation schedule are not subjected to positional correction using a correlation value of the images as a whole, but instead so that positional correction is performed using a correlation function weighted according to an image feature of an object included in a field of view.

FIG. 5 is a block diagram schematically showing the image-processing device 100 for performing positional correction. The image-processing device 100 (101 through 103), is configured by the CPU 61 reading an image-processing program GP (GP1 through GP3) configured and stored in advance in the ROM 62, and the CPU 61 executing a process based on the image-processing program GP. FIG. 1 is a flowchart showing the image-processing program GP1 according to a first embodiment.

The image-processing device 100 comprises: an image analyzing part 110 for analyzing, from the first image and the second image captured by the imaging device (54c, 55c) at a predetermined observation interval, an image feature of each of the objects included in each of the images; a positional correction value calculating part 120 for calculating a positional correction value for correcting a relative shift in the position in which the first image and the second image are captured, using a correlation function weighted according to the analyzed image feature of each of the objects; and an inter-image alignment part 130 for performing, based on the positional correction value calculated by the positional correction value calculating part, a positional correction between the first image and the second image; a time-lapse image being generated using the first image and the second image between which the positional correction has been performed by the inter-image alignment part.

First Embodiment

The image-processing device 101 according to the first embodiment is configured by the CPU 61 executing the image-processing program GP1 according to the first embodiment. The image-processing device 101 uses a feature based on the external profile of an object included in the first image and the second image as a basis for an image feature of the object, and performs positional correction on a positional shift using a correlation function weighted according to the feature.

According to the image-processing program GP1, first, the first image at time t and the second image at time t+1 stored in the RAM 63 are read and acquired in step S110, and segmented into regions in step S120. The segmentation may be performed using a variety of known methods, such as binarization by luminance value; binarization by dispersion value; snakes or level set methods, or another dynamic contour extraction method.

Next, a feature based on the external profile of each segmented region (i.e., shape feature) is analyzed in step 130. Examples of a feature based on the external profile include the width or length of the region, area (i.e., size), and complexity of the shape (perimeter$^2$/area). In the embodiment, a description will be given regarding an instance wherein the emphasis is directed on the contact area of the cell, and the area of the region is specified as the feature based on external profile. A frequency distribution of the area of each of the segmented regions is created in step S135, and the process advances to step S140.

In step S140, it is determined whether the frequency distribution created in step S135 can be modeled by one normal distribution. In an instance where the frequency distribution can be expressed using one normal distribution, the process advances to step S150A; in an instance where the frequency distribution cannot be modeled by a single normal distribution, but is instead expressed by a sum of a plurality of normal distributions, the process advances to step S150B. For example, in an instance of the image shown in FIG. 4, the frequency distribution created in step S135 is expressed by two distributions, namely the distribution of cells C1 having a large contact area and the distribution of cells C2 having a small contact area; therefore, the process advances to step S150B.

In step 150A, each of the segmented regions is labeled, the area of each of the regions is calculated, and a weight of each of the regions is specified in step S155A according to the area value. Meanwhile, in step 150B, the regions are classified according to a separated distribution (e.g., into a classification for cells C1 having a large contact area and a classification for cells C2 having a small contact area), and the weight of each of the classifications is specified in step 155B.

Figures 6A, 6B:
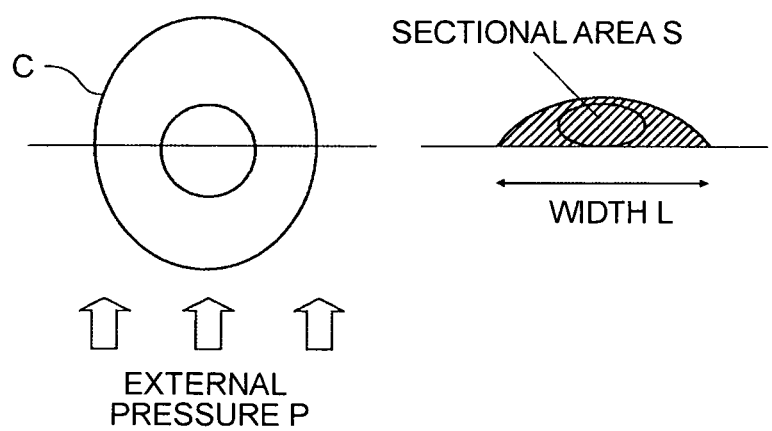
FIG. 6 is a plan view and a cross-sectional view schematically showing a state in which external pressure is acting on a cell.

The weight function will now be discussed. FIG. 6 is a plan view (1) and a cross-sectional view (2) schematically showing a state in which an external pressure P is acting on a cell C from the bottom of the drawing. In an instance where a constant external pressure P is acting on the cell C representing the observed object, an external force (a force acting to move the cell) $F_j$ applied by the external pressure P on a desired cell $C_j$ is $F_j \propto P \times S_j$, where $S_j$ is the cross-sectional area of a surface perpendicular to the external pressure P. The force is proportional to the cross-sectional area $S_j$ of the cell $C_j$. In an instance where the cell C is a monolayer cell, the thickness of a nuclear cell is constant; therefore, taking $L_j$ to be the width in a direction orthogonal to the external pressure P, the relationship $F_j \propto P \times L_j$ obtains, and the external force $F_j$ applied by the external pressure P on the cell $C_j$ is proportional to the width $L_j$.

Meanwhile, the mass W of the cell is proportional to the volume V. When the three-dimensional shape of the cell is approximated to a cylinder having a diameter $L_j$, the volume Vj is proportional to the square of the diameter, or to the value of the square of width $L_j$ of the cell $C_j$ in a direction orthogonal to the external pressure. The frictional force (frictional resistance: $\mu W_j$) on the cell in contact with the culture container 10 is therefore proportional to $L_j^{-2}$.

Therefore, the degree of influence of the external pressure P on the movement of the cell (i.e., the susceptibility of the cell to the external pressure P) decreases in proportion to $L_j^{-1}$ even when only a simple frictional force is taken into account, the cell becoming less susceptible to the effect of external pressure P with increasing cell size. In reality, the friction coefficient $\mu$ also varies according to the contact area of the cell, so the weight function is a function that is steeper than $L^{-1}$.

A weight function $g_j$, calculated according to the considerations described above, and used for weighting according to the size of the contact area of the cell, is configured and stored in advance in the ROM 62. The weight function $g_j$ that corresponds to the size of the cells $C_j$ or the mean size in each of the classifications is specified in steps S155A and S155B. The process then moves to step S170.

In step S170, there is created a map of the weight function $g_j$ specified for each region. In step S180, the weight function value is used to calculate a correlation value between the first image at time t and the second image at time t+1. The amount of movement between images that corresponds to the total sum of correlation values being at a maximum is taken to be the amount of movement caused by the positioning error and is stored in the RAM 63 as a positional correction amount between the first image and the second image (i.e., the value for correcting the position of the second image relative to the first image). The process then moves to step S190.

In step S190, positional correction between the first and second images is performed on the basis of the positional correction amount calculated in step S180. In an instance where, for example, a command to generate a time-lapse image is inputted from the control panel 71 into the CPU 61, a time-lapse image is generated using the position-corrected first and second images. In an instance where a selection is made in the control panel 71 to perform a process of calculating the amount of movement of each of the cells, and the corresponding command is inputted into the CPU 61, the amount of movement of each of the cells between the position-corrected first and second images is calculated, and displayed, for example, as a vector using the direction and length of an arrow as shown in FIG. 4.

In the image-processing device 101 configured by executing such an image-processing program GP1, a feature based on the external profile of the object is extracted as the image feature of the object, a weight according to the feature is applied to calculate the correlation between a plurality of images, a movement amount corresponding to the total sum of the correlation values being at a maximum is calculated as a positional correction amount, and image-processing between a plurality of images is performed. Therefore, even in an instance where foreign objects, bubbles, or other articles that do not form part of the observed object, or a plurality of observed object cells having varying dynamic characteristics, are included in the observation field of view, it is possible to perform precise positional correction, thereby making it possible to increase the accuracy of positional correction between intermittently captured images.

Second Embodiment

Figure 7:
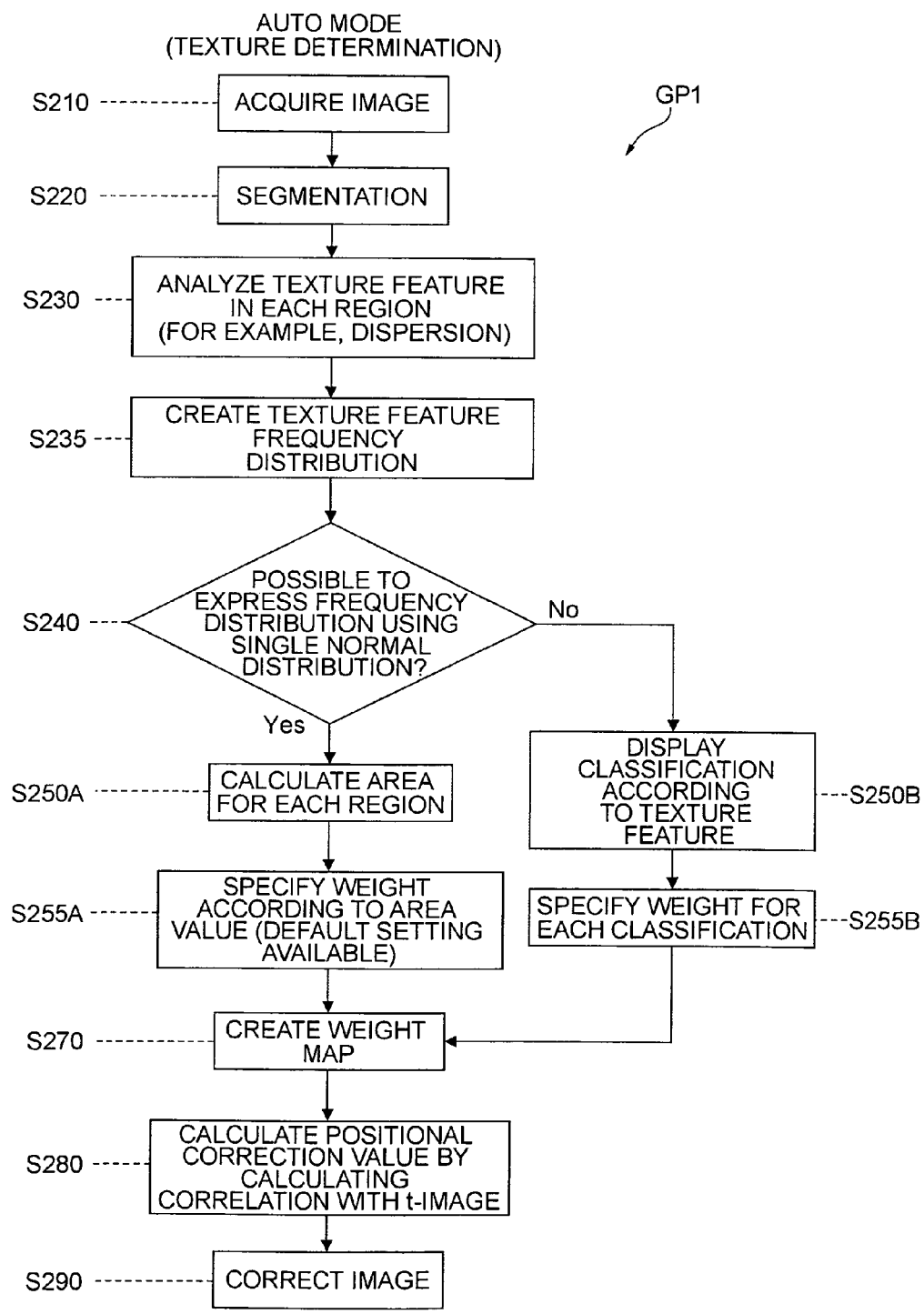
FIG. 7 is a flowchart showing an image-processing program according to a second embodiment.

An image-processing device 102 according to a second embodiment will now be described. The image-processing device 102 according to the present embodiment uses a feature of the texture of an object located in a field of view as a basis for the image feature of the object. In other words, the configuration of the image-processing device as a hardware resource is similar to that of the image-processing device 101 according to the first embodiment; however, the image feature to be determined in the image-processing procedure is different from that according to the image-processing device 101 in the first embodiment. Shown in FIG. 7 is a flowchart of an image-processing program GP2 that is read by the CPU 61 to constitute the image-processing device 102. An image-processing method according to the present embodiment will now be described, following the processing flow of the image-processing program GP2.

According to the image-processing program GP2, first, the first image at time t and the second image at time t+1 stored in the RAM 63 are read and acquired in step S210, and segmented into regions in step S220. The segmentation may be performed using a variety of methods, as with the instance previously described.

Next, a feature based on the texture of each segmented region (i.e., texture feature) is analyzed in step 230. Examples of a feature based on the texture include pattern or dispersion of the segmented regions and presence of a nucleus. In the embodiment, a description will be given regarding an instance wherein the emphasis is directed on dispersion of the cell image, and the region dispersion is specified as the feature based on the texture. A frequency distribution of the dispersion of each of the segmented regions is created in step S235, and the process advances to step S240.

In step S240, it is determined whether the frequency distribution created in step S235 can be modeled by one normal distribution. In an instance where the frequency distribution can be expressed using one normal distribution, the process advances to step S250A; in an instance where the frequency distribution cannot be modeled by a single normal distribution, but is instead expressed by a sum of a plurality of normal distributions, the process advances to step S250B.

In step 250A, each of the segmented regions is labeled, the area of each of the regions is calculated, and a weight of each of the regions is specified in step 255A according to the area value. Meanwhile, in step 250B, the regions are classified into a plurality of classifications for each normal distribution (e.g., classified into three classifications according to the dispersion value, from a classification for cells having a large dispersion value to a classification for cells having a small dispersion value), and the weight of each of the classifications is specified in step 255B.

As with the first embodiment, a weight function $g_j$ according to the size (or the classification) of the contact area of each cell may be used as the weight function. In an instance where the feature of the texture is divided into a plurality of classifications, wherein the division arises from a difference in the type or growing stage of each of the cells, a weight function according to the respective dynamic characteristics may be used. A weight function established according to the considerations described above is stored in advance in the ROM 62. The weight function is specified in steps S255A and S255B. The process then moves to step S270.

In step S270, there is created a map of the weight function specified for each region. In step S280, the weight function value is used to calculate a correlation value between the first image at time t and the second image at time t+1. The amount of movement between images that corresponds to the total sum of correlation values being at a maximum is taken to be the amount of movement caused by the positioning error and is stored in the RAM 63 as a positional correction amount between the first image and the second image. The process then moves to step S290.

In step S290, positional correction between the first and second images is performed on the basis of the positional correction amount calculated in step S280. In an instance where a command to generate a time-lapse image or a command to calculate the amount of movement of the cells is inputted from the control panel 71 into the CPU 61, the CPU 61 generates a time-lapse image using the position-corrected first and second images, or displays the amount of movement of each of the cells as a vector using an arrow as shown in FIG. 4.

In the image-processing device 102 configured by executing the image-processing program GP2 as described above, a feature based on the texture of the object is extracted as the image feature of the object, a weight according to the feature is applied to calculate the correlation between a plurality of images, a positional correction amount is calculated, and image-processing between a plurality of images is performed. Therefore, even in an instance where foreign objects, bubbles, or other articles that do not form part of the observed object, or a plurality of observed object cells having varying dynamic characteristics, are included in the observation field of view, it is possible to perform precise positional correction, thereby making it possible to increase the accuracy of positional correction between intermittently captured images.

Third Embodiment

An image-processing device 103 according to a third embodiment will now be described. As shown by a long-dashed double-short-dashed line in FIG. 5, The image-processing device 103 is configured so as to have, in addition to the image-processing device 101, 102 according to each of the embodiments described above, a feature memory part 140 for storing a plurality of types of features with regards to the image feature, and a mode selection switch 150 for selecting the type of feature stored in the feature memory part 140. The positional correction value calculating part 120 calculates a positional correction value using a correlation function weighted according to the feature selected using the mode selection switch 150.

Shown in FIG. 8 is a flowchart of an image-processing program GP3 that is read by the CPU 61 to constitute the image-processing device 103. An image-processing method according to the present embodiment will now be described, following the processing flow of the image-processing program GP3.

According to the image-processing program GP3, first, the first image at time t and the second image at time t+1 stored in the RAM 63 are read and acquired in step S310, and segmented into regions in step S320. The segmentation may be performed using a variety of methods, as with the instance previously described.

Next, in step S330, a target to be weighted is extracted and designated from the image that has been segmented into regions. For example, a cell C1 having a large area in the image shown in FIG. 4 is extracted and designated for weighting. The process then moves to step S340.

In step S340, a decision is made as to whether there exists another target to be weighted, other than the target designated as described above, in the first image and the second image acquired from the RAM 63. In an instance where it is determined that another region to be weighted exists in addition to the designated target, such as in an instance where a cell C2 having a small area exists in addition to the cell C1 designated in step S330, the process advances to step S345; in an instance where it is determined that no such region exists, the process advances to step S370.

In step S345, a mode selection screen for selecting a type of feature configured in the feature memory part 140 is displayed on the display panel 72. The image acquired from the RAM 63 is displayed on the mode selection screen, with the designated target extracted in step S330 (i.e., cell C1) and the other region to be weighted (i.e., cell C2) identified. Modes that can be selected using the mode selection screen can be configured as appropriate according to the selection of the features; for example, a manual mode, a shape feature mode, and a texture feature mode are configured as shown in FIG. 8. An operator of the cell culture observation system can operate the mode selection switch 150 and perform a positional correction process using a desired mode.

In an instance where the manual mode is selected using the mode selection switch 150, the manual mode is configured in step S346 and the process returns to step S330. The operator may then operate the control panel 71 and manually add or remove a designated region to be weighted.

In an instance where the shape feature mode is selected using the mode selection switch 150, the process advances to step S350A, the shape feature mode is configured, and classification is performed according to the shape feature. For example, as described in relation to the image-processing device 101 of the first embodiment, the segmented regions are classified into a classification for cells C1 having a large contact area and a classification for cells C2 having a small contact area.

In an instance where the texture feature mode is selected using the mode selection switch 150, the process advances to step S350B, the texture feature mode is configured, and classification is performed according to the texture feature. For example, as described in relation to the image-processing device 102 of the second embodiment, the segmented regions are classified into a plurality of classifications, from a classification for cells having a large dispersion value to a classification for cells having a small dispersion value.

A region in the same classification as the designated region is added to the regions to be weighted in step S360, whereupon the weight function is specified, and a weight map is created, in step S370. For the weight function, a weight function $g_j$ corresponding to the size of the contact area or classification of each cell may be used as with the previously described image-processing device 101 and the image-processing device 102; or, in an instance where classification is performed according to a difference in the type or the growing stage of each of the cells, a weight function corresponding to the respective characteristics may be used.

When the weight function map is created in step S370, the weight function value is used to calculate a correlation value between the first image at time t and the second image at time t+1 in step S380. The amount of movement between images that corresponds to the total sum of correlation values being at a maximum is taken to be the amount of movement caused by the positioning error and is stored in the RAM 63 as a positional correction amount between the first image and the second image. The process then moves to step S390.

In step S390, positional correction between the first and second images is performed on the basis of the positional correction amount calculated in step S380. In an instance where a command to generate a time-lapse image, or a command to calculate the amount of movement of the cells, is inputted from the control panel 71 into the CPU 61, the CPU 61 generates a time-lapse image using the position-corrected first and second images, or displays the amount of movement of each of the cells as a vector using an arrow as shown in FIG. 4.

In the image-processing device 103 configured by executing the image-processing program GP3 as described above, a plurality of types of feature are configured in advance and stored in the feature memory part 140 as the image feature of the object, a weight that corresponds to the feature selected using the mode selection switch 150 is applied to calculate the correlation between a plurality of images, a positional correction amount is calculated, and image-processing between a plurality of images is performed. Therefore, even in an instance where foreign objects, bubbles, or other articles that do not form part of the observed object, or a plurality of observed object cells having varying dynamic characteristics, are included in the observation field of view, it is possible to select a suitable feature according to the type or state of the observed object and perform precise positional correction, thereby making it possible to increase the accuracy of positional correction between intermittently captured images.

As described above, according to the image-processing program GP (GP1 through GP3) of the present invention, and the image-processing method and the image-processing device 100 (101 through 103) configured by executing the image-processing program, positional correction is performed between images using a weight correlation function that corresponds to an image feature of an object in the field of view. It is accordingly possible to obtain image-processing means for processing time-lapse images in which an enhancement is made to the accuracy of positional correction between each of the intermittently captured images.

Each of the embodiments describes an example of an instance in which the image-processing device used for time-lapse images according to the present invention is applied to a cell culture observation system, but the present invention is not limited to the embodiments described. The present invention can be similarly applied to another device for acquiring a plurality of images at a predetermined time interval and continuously reproducing the images, and a similar effect can be obtained. An observation device for observing the state of movement of marine vessels in a sea region is used to provide a brief description by way of example. Examples of a feature based on external profile include vessel type (angling boat, passenger ferry, tanker, destroyer, etc.), size (displacement), and height; examples of a feature based on texture include color of vessel and dispersion; and examples of an external pressure include sea current and wind state. Examples of other devices include a road information observation apparatus for observing traffic conditions and a monitoring apparatus for monitoring flow of people or a similar situation.

What is claimed is:

1. An image-processing method for processing a time-lapse image, comprising:
   acquiring a first image obtained by using an imaging device to capture an image of a plurality of objects located within a field of view, and a second image obtained by using the imaging device to capture an image of the objects located within the field of view after a predetermined time period has elapsed;
   calculating, executed by a processor, a positional correction value to be used for a relative shift in the position in which the first image and the second image are captured by using a correlation function weighted according to an image feature of each of the objects included in the first image and the second image; and
   performing a positional correction between the first image and the second image based on the positional correction value, and generating a time-lapse image.

2. The image-processing method for processing a time-lapse image according to claim 1, wherein the image feature is a feature based on an external profile of each of the objects.

3. The image-processing method for processing a time-lapse image according to claim 1, wherein the image feature is a feature based on a texture of each of the objects.

4. An image-processing program on a non-transitory computer readable medium for processing a time-lapse image, comprising the steps of:
   acquiring a first image obtained by using an imaging device to capture an image of a plurality of objects located within a field of view and a second image obtained by using the imaging device to capture an image of the plurality of objects located within the field of view after a predetermined time period has elapsed;
   calculating a positional correlation value to be used for a relative shift in the position in which the first image and the second image are captured by using a correlation function weighted according to an image feature of each of the objects included in the first image and the second image;
   performing a positional correction between the first image and the second image based on the calculated positional correction value; and
   generating a time-lapse image using the first image and the second image between which the positional correction has been performed.

5. The image-processing program for processing a time-lapse image according to claim 4, wherein the image feature is a feature based on an external profile of each of the objects.

6. The image-processing program for processing a time-lapse image according to claim 4, wherein the image feature is a feature based on a texture of each of the objects.

7. The image-processing program for processing a time-lapse image according to claim 4, wherein
   the image feature comprises a plurality of types of features configured and stored in advance,
   the image-processing program has a mode selection step for selecting the type of feature, and
   the image-processing program calculates the shift amount using a weight correlation function that corresponds to the feature selected in the mode selection step.

8. An image-processing device for processing a time-lapse image, comprising:
   an imaging device capturing an image of a plurality of objects;
   an image analyzing part analyzing, from a first image and a second image captured by the imaging device at a predetermined time interval, an image feature of each of the objects included in each of the images;
   a positional correction value calculating part calculating a positional correction value to be used for a relative shift in the position in which the first image and the second image are captured, using a correlation function weighted according to the analyzed image feature of each of the objects; and
   an inter-image alignment part performing, based on the positional correction value calculated by the positional correction value calculating part, a positional correction between the first image and the second image, wherein a time-lapse image is generated using the first image and the second image between which the positional correction has been performed by the inter-image alignment part.

9. The image-processing device for processing a time-lapse image according to claim 8, wherein the image feature is a feature based on an external profile of each of the objects.

10. The image-processing device for processing a time-lapse image according to claim 8, wherein the image feature is a feature based on a texture of each of the objects.

11. The image-processing device for processing a time-lapse image according to claim 8, further comprising:

a feature memory part storing a plurality of types of features configured in advance with regards to the image feature; and mode selection means for selecting the feature type configured in the feature memory part, wherein the positional correction value calculating part calculates the positional correction value using a weight correlation function that corresponds to the feature selected in the mode selection means.

12. An observation system comprising:

an observation unit to observe a plurality of objects; and an image-processing device to process a time-lapse image, comprising:

an imaging device capturing an image of the plurality of objects;

an image analyzing part analyzing, from a first image and a second image captured by the imaging device at a predetermined time interval, an image feature of each of the objects included in each of the images;

a positional correction value calculating part calculating a positional correction value to be used for a relative shift in the position in which the first image and the second image are captured, using a correlation function weighted according to the analyzed image feature of each of the objects; and an inter-image alignment part performing, based on the positional correction value calculated by the positional correction value calculating part, a positional correction between the first image and the second image, wherein a time-lapse image is generated using the first image and the second image between which the positional correction has been performed by the inter-image alignment part.

* * * * *